United States Patent
Berglof et al.

(10) Patent No.: US 7,682,510 B2
(45) Date of Patent: Mar. 23, 2010

(54) METHOD OF STERILIZATION

(75) Inventors: Jan Berglof, Uppsala (SE); Ingrid Drevin, Uppsala (SE); Ola Lind, Uppsala (SE); Ulf Segerbo, Uppsala (SE)

(73) Assignee: GE Healthcare Bio-Sciences AB, Uppsala (SE)

( * ) Notice: Subject to any disclaimer, the term of this patent is extended or adjusted under 35 U.S.C. 154(b) by 0 days.

(21) Appl. No.: 11/817,268

(22) PCT Filed: Mar. 6, 2006

(86) PCT No.: PCT/SE2006/000284

§ 371 (c)(1), (2), (4) Date: Aug. 28, 2007

(87) PCT Pub. No.: WO2006/096116

PCT Pub. Date: Sep. 14, 2006

(65) Prior Publication Data

US 2008/0142439 A1    Jun. 19, 2008

(30) Foreign Application Priority Data

Mar. 7, 2005    (SE) .................................... 0500554
Mar. 6, 2006    (WO) ................ PCT/SE2006/000284

(51) Int. Cl.
   *B01D 15/08*    (2006.01)

(52) U.S. Cl. ................. 210/635; 210/656; 210/764; 210/198.2

(58) Field of Classification Search ............. 210/635, 210/656, 659, 764, 198.2, 282; 96/101, 105
See application file for complete search history.

(56) References Cited

U.S. PATENT DOCUMENTS

| | | | | |
|---|---|---|---|---|
| 2,748,057 A | * | 5/1956 | Goren | 208/6 |
| 4,028,242 A | * | 6/1977 | Kokurin et al. | 210/774 |
| 4,484,061 A | * | 11/1984 | Zelinka et al. | 392/480 |
| 4,627,918 A | * | 12/1986 | Saxena | 210/656 |
| 4,676,898 A | * | 6/1987 | Saxena | 210/198.2 |
| 4,684,531 A | * | 8/1987 | Torterotot | 426/399 |
| 4,865,729 A | * | 9/1989 | Saxena et al. | 210/198.2 |
| 4,923,068 A | * | 5/1990 | Crowson | 210/741 |
| 5,268,097 A | * | 12/1993 | Girot et al. | 210/198.2 |
| 5,268,144 A | * | 12/1993 | Heilmann et al. | 422/26 |
| 5,367,054 A | * | 11/1994 | Lee | 530/359 |
| 5,423,982 A | * | 6/1995 | Jungbauer et al. | 210/198.2 |
| 5,676,837 A |   | 10/1997 | Jungbauer et al. | |
| 5,817,528 A | * | 10/1998 | Bohm et al. | 436/529 |
| 5,906,747 A | * | 5/1999 | Coffman et al. | 210/635 |
| 6,103,112 A | * | 8/2000 | Sutton et al. | 210/198.2 |
| 2006/0054558 A1 | * | 3/2006 | Jones et al. | 210/656 |

OTHER PUBLICATIONS

Hermanson, G. T., Mallia, A. K., & Smith, P. K. (1992). "Immobilized Affinity Ligand Techniques" (p. 118). San Diego, CA: Academic Press.

Hjerten, S. (1964). "The Preparation of Agarose Spheres for Chromatography of Molecules and Particles". Biochimica et Biophysica Acta, 79, 393-398.

Janson, J.-C., & Ryden, L. (Ed.) (1998). "Protein Purification. Principles, High-Resolution Methods, and Applications". John Wiley & Sons, Inc.

Meyer, V. (1993). "Practical High-Performance Liquid Chromatography". (p. 39-40). John Wiley & Sons, Inc.

* cited by examiner

*Primary Examiner*—Ernest G Therkorn
(74) *Attorney, Agent, or Firm*—Yonggang Ji (57) ABSTRACT

The present invention relates to a method of sterilizing a chromatography column which is packed with a separation matrix, which method comprises passing a superheated aqueous liquid through the packing of the column to obtain at least one substantially sterile packed chromatography column. The method may also comprise a preceding heating. In the most advantageous embodiment, the superheated aqueous liquid is passed in a substantially uniform flow through the packing of the column, resulting in a sterility of the packed column.

14 Claims, 7 Drawing Sheets

METHOD OF STERILIZATION

CROSS-REFERENCE TO RELATED APPLICATIONS

This application is a filing under 35 U.S.C. §371 and claims priority to international patent application number PCT/SE2006/000284 filed Mar. 6, 2006, published on Sep. 14, 2006, as WO 2006/096116, which claims priority to patent application number 0500554-1 filed in Sweden on Mar. 7, 2005; the disclosures of which are incorporated herein by reference in their entireties.

TECHNICAL FIELD

The present invention relates to a method of sterilizing a packed chromatography column. The invention also encompasses a system for the sterilization of packed chromatography columns, use of such sterilized packed chromatography columns in the purification of biomolecules as well as sterile packed chromatography columns as such.

BACKGROUND OF THE INVENTION

The rapid development of biotechnological methods for the manufacture of biomolecules, such as proteins and peptides, also put new requirements on the equipment used in such processes. For example, in the pharmaceutical industry, the end product must meet certain demands on purity and safety to be approved as a drug by the authorities. A process for preparation of biomolecules usually involves a number of purification steps, such as filtration, precipitation, chromatography etc. Liquid chromatography is a well known and much used technique, which may briefly be described as the fractionation of components of a mixture based on differences in the physical or chemical characteristics of the components. More specifically, in chromatography, two mutually immiscible phases are brought into contact wherein one phase, commonly known as the matrix or a resin, is stationary and the other one is mobile. The sample mixture, introduced into the mobile phase, undergoes a series of interactions between the stationary and mobile phases as it is being carried through the system by the mobile phase. Interactions which exploit differences in the physical or chemical properties of the components in the sample govern the rate of migration of the individual components moving through a column. Due to high versatility, chromatography is commonly used in biotechnological processing and any other method where it is desired to separate out one or more useful components from a fluid mixture that contains other components, which may not be useful or are less valuable. Thus, chromatography is useful e.g. in methods that involve removal and/or isolation of viruses, nucleic acids, pyrogens, fine chemicals, food additives, diagnostics and drugs.

A conventional process for the preparation of biomolecules, such as proteins and peptides, commonly includes an initial cleaning in place (cip) sanitization of vessels, filters, chromatography columns etc, commonly by a solution of sodium hydroxide, and subsequently operating while maintaining as low a bioburden as possible. To obtain a sterile product, very clean conditions are maintained until the last step, which involves passing the product through a sterile filter into a sterile container.

However, a well known problem of such a conventional process is that products having a distinct large three-dimensional structure, such as large DNA molecules, virus, and protein complexes, cannot be sterile filtered without impairing recovery. For example, commonly sterile filters have pore sizes of 0.22 µm, while e.g. vaccinia viruses, rod-like viruses, have diameters up to 260 nm and can be up to 700 µm long. Alternative ways of sterilizing the products are known, such as addition of chemicals or autoclaving. However, due to the high purity requirements, addition of chemicals is usually avoided in the biotechnical preparation of drug molecules. Further, autoclaving will involve temperatures and pressures which would readily kill living organisms, or at least make substantial changes to their conformation thus eradicating their biological activity, and is consequently not suitable for products such as virus and plasmids.

An alternative to the above-discussed sterilization of the end product would be to run the whole process starting from sterile raw materials, and using previously sterilized equipment. "Equipment" in this context would include fermenter, commonly containing the fermentation broth, tubings, other vessels, filters, centrifuges, chromatography columns and the like. One of the most frequently method used for sterilization of process equipment in general is autoclaving, and of the above, fermenters, optionally filled with broth, are commonly autoclaved without any serious problems, provided their size allows easy movement thereof. In general, tubings, vessels and filters are also easily autoclavable. A specific case of filters known as hollow fibres, wherein a thin layer of resin has been immobilised to the inside of a hollow fibre, have been sterilized with steam and/or hot water, but have also successfully been autoclaved. This is mainly because the layer of resin in a hollow fibre is thin enough not to impose any problems with regard to uniformity and packing properties.

However, the process of autoclaving is more complex with regard to the chromatography equipment. Firstly, in large scale processing, chromatography columns will often be of a size which is not readily moved into an autoclave. Secondly, the pressure within a closed vessel, such as a packed chromatography column, in an autoclave may impose serious problems, for example as regards uniformity and other properties of the packing. For that reason, the sterilization of chromatography columns and chromatography matrices are commonly carried out separately, which means that a subsequent step for packing the column will be required. In addition to being time consuming and hence costly, such a packing may be difficult to ensure in practise without contamination. Thirdly, due to the low heat transport in the resin during autoclaving, sterilization would require a very long treatment time, and will in some cases still not be properly achieved throughout the matrix.

An example of separate sterilization of different components is disclosed in U.S. Pat. No. 5,817,528 (Böhm et al), which relates to a method for producing a sterile and pyrogen-free column that contains coupled protein intended for use in removing a predetermined substance from the blood of a human subject. According to U.S. Pat. No. 5,817,528, sterilization of the finished protein-containing product is achieved by providing sterile and pyrogen-free raw materials at each production step. More specifically, the method provides a pathogen-free, purified protein solution; and a sterile and pyrogen-free column matrix material, such as an agarose. The sterile and pyrogen-free, activated matrix material and the pathogen-free, purified protein solution are then combined under aseptic conditions to effect the binding of the protein to the matrix material, and the protein-coupled matrix material is filled under aseptic conditions into a sterile and pyrogen-free housing to produce a sterile and pyrogen-free column.

However, such a process will require a number of process steps, which is disadvantageous in an industrial process since each step will increase the total costs.

Sterilization of a packed chromatography column is disclosed in U.S. Pat. No. 5,423,982 (Jungbauer et al), which relates to a liquid chromatography column well-suited for in situ sterilization effected by washing with a sterilization solution. A specific arrangement in the chromatography column, including a multilayered sintered metal filter and a corrugated expanding ring at the outlet, is stated to reduce or eliminate the "dead spaces" where microbes can become secluded from sterilizing solutions. The sterilizing solution used in U.S. Pat. No. 5,423,982 on a packed bed contain 1500 ppm peracetic acid as sterilizing agent.

Another example of chemical sterilization is disclosed in U.S. Pat. No. 5,676,837 (Jungbauer et al), which relates to a method for sterilization liquid chromatography resins that are highly resistant to oxidation by strongly oxidizing agents. According to U.S. Pat. No. 5,676,837, one example of a commonly used sterilizing agent is ethanol/water at a neutral or acidic pH, a common concentration being about 20% ethanol. However, as is well known, 20% ethanol has no sporocidal effect, and is therefore not completely sterilizing, and in addition large molecular aggregates may be destabilized by such a treatment. U.S. Pat. No. 5,676,837 states that a commonly used sterilization technique for instruments and the like, namely destroying microbes by wet heat, has not been employed to sterilize chromatographic resins due to their common temperature sensitivity. To avoid drawbacks such as the above, U.S. Pat. No. 5,676,837 suggests a method of sterilizing a chromatography resin by washing it with an aqueous solution of a percarboxylic acid which solution also contains an acetate buffer in a concentration of about 0.1-2M. The sterilization can be performed in a separate vessel or, alternatively, by pouring the solution through the packed chromatography column.

In summary, it is concluded that there is still a need in this field of robust methods for sterilization including spore destruction of chromatography columns, in particular in the context of processes for the manufacture of large targets, such as viral vectors and plasmid DNA. More specifically, there is a need for a sterile packed chromatography column which is adaptable to a sterile process.

BRIEF DESCRIPTION OF THE INVENTION

The present invention relates to cleaning and sterilization of packed chromatography columns. One aspect of the invention is to provide a novel method for sterilization of packed chromatography columns. This can be achieved by applying an aqueous liquid combined with pressure and heat to the packed chromatography column.

Another aspect is to provide such a method, which avoids the addition of chemicals; which does not impair the packing properties of the matrix; and/or which does not harm the binding properties of a functionalised chromatography matrix.

Another aspect of the invention is to provide a novel system for sterilizing chromatography columns, especially for large scale processing. A specific aspect is to provide such a sterilized system, which enables purification of large products under sterile conditions.

A further aspect is to provide a sterile packed chromatography column.

Further aspects and advantages of the present invention will appear from the detailed description that follows.

BRIEF DESCRIPTION OF THE DRAWINGS

FIG. 1 shows that the column is packed, connected to a system where a flow is initiated and finally that heat and pressure are applied.

FIG. 2 shows how liquid can be pumped into the chromatography column (extraction cell), how it can be heated in the oven and how the liquid can be withdrawn at the bottom of the column and collected in a vial.

FIG. 3 shows results of the pressure/flow tests performed in example 2 below. More specifically.

FIG. 4 shows the chromatography elution profile of a mixture of 3 proteins. The filled line represents the untreated medium and the dotted line the ASE treated medium. Retention times of the different proteins are identical on both media, indicating an identical functional behaviour.

FIG. 5 shows the system used for heat sterilization according to the invention as described in Example 5 below. Vessel (1) contains the solution used for sterilization. The fluid passes through a valve (V1) to a piston pump (P1). The pump has high flow accuracy therefore we don't need any flow meter. The buffer passes through an electric heat exchanger (H1). A sensor (S2) gives feedback to the regulator controlling the heat exchanger (H1). Another sensor (S1) is used to adjust the pressure delivered by a valve (V5). Before the column (C1), there is a security relief valve to avoid over pressure. The column (C1) is equipped with an electrical heating jacket (H2). A further sensor (T3) gives feed back to a regulator controlling (H2). A sensor (S4) is motoring the outlet temperature. A cooler (H3) cools the buffer to room temperature before it leaves the system through a pressure valve (V5). All equipment heated is insulated.

DEFINITIONS

The term "packed" in the context of a chromatography column means that a vessel is substantially filled with stationary phase, also known as chromatography resin, separation matrix or media. Furthermore, "packed" assumes a plate number and an asymmetry that is generally accepted to indicate a homogeneous and steady flow throughout the complete columns, as understood by the skilled person in this field (see e.g. "Protein Purification" Ed. Jan-Christer Jansson & Lars Rydén; and "Practical High-Performance Liquid Chromatography", Veronika R. Meyer, 2nd edition, 1993, Ed. John Wiley & Sons, p. 39-40).

The term "superheated" liquid means a liquid that has been heated above the boiling point without converting into vapour.

The term "biomolecules" as used herein comprises proteins; such as enzymes and antibodies; peptides; nucleic acids, such as DNA, RNA and PNA; viruses; cells and cell components.

The term "bioburden" means a population of viable microorganisms on a product and/or package.

The term "$F_O$" value is used in accordance with its standard definition in the field of microbiology. For example, a sterilising at 121° C. for 15 minutes gives an $F_0$ value of 15 minutes. Thus, the F0 value is a reference value designating the time at 121.1° C. (250° F.) required to destroy a specific number of organisms whose z value is 10° C. (18° F.) which is the z value for *Clostridium botulinum*. The D value represents the time in minutes at a specified temperature necessary to kill 90% (1 log 10 cycle) of the bacterial population (either vegetative cells or spores), and the z value corresponds to the number of degrees (temperature) required for a specific thermal death time curve to pass through one log cycle of D values. The F value equals the number of minutes at a specific temperature required to destroy a specified number of organisms having a specific z value. The F value is thus a measure of the capacity of a heat treatment to sterilize.

The term "ligand" means herein a functional group or molecule capable of interacting with a target compound. In chromatography matrices, a plurality of ligands are attached to a porous or non-porous support via linkers or longer elements known as spacers. Commonly known ligands comprise charged groups (ion exchange ligands); hydrophobic groups; groups capable of chelating metals (IMAC ligands); and groups with biological affinity to a specific target, such as antibody-antigen interaction (affinity ligands). Mixed mode ligands are also well known, which comprise two or more different such interacting groups, such as a hydrophobic entity and a charged entity.

DETAILED DESCRIPTION OF THE INVENTION

In a first aspect, the present invention relates to a method of sterilizing at least one chromatography column packed with a separation matrix, which method comprises passing a superheated aqueous liquid through the packing of said column(s) to obtain at least one substantially sterile packed chromatography column. In a specific embodiment, the column is sterile after passage of the superheated liquid.

An advantageous embodiment is a method of sterilizing at least one chromatography column packed with a separation matrix, which method comprises heating an aqueous liquid to a temperature which under the prevailing pressure provides a superheated aqueous liquid; and passing said superheated aqueous liquid through the packing of the column to obtain at least one substantially sterile packed chromatography column. In this context, it is understood that the aqueous liquid is heated to the temperature at which is becomes superheated.

As is readily recognised by the skilled person in this field, the duration of the treatment with superheated aqueous liquid, i.e. the contact time between separation matrix and superheated aqueous liquid, required for an efficient sterilisation will depend on the nature of the contaminant to be removed. For example, some bacteria are more sensitive than others to heat treatment, and other contaminants such as spores will in general require harsher conditions to be destroyed completely. In an advantageous embodiment, the liquid flow results in a sterility of the packed column that satisfies the $F_O$ requirements for the system in question. In one embodiment, the method comprises passing the superheated aqueous liquid in a substantially uniform flow through the packing of the column.

Thus, the present method is useful on any size of chromatography column, and eliminates the need of packing a sterile column with a sterile chromatography matrix, as discussed above. It is a simple method which is easily applicable in automated systems. In a specific embodiment, the invention relates to disinfection of a packed chromatography column by passing a superheated aqueous liquid across the column.

As is easily understood by the skilled person in this field, the appropriate temperature and pressure will vary depending on the specific aqueous liquid used in each case, such as the buffering components of a buffer. However, phase diagrams are readily available from standard text books, and indicate suitable pressure/temperature ranges and values for standard aqueous liquids. Thus, the temperature of the aqueous liquid is maintained at a temperature that provides, at the existing pressure, a superheated liquid that provides sterilization of all of the column and its packing. The temperature is preferably above 100° C. and may be in a range of 100-150° C., such as 100-140 and preferably 110-130° C. Similarly, depending on the temperature, the pressure may be in a range of 0-35 bar, such as 1-20, preferably 1-15, and more preferably 1-3 bar above atmospheric pressure. In a specific embodiment, the pressure is about 1 bar above atmospheric pressure.

In one embodiment, the liquid is maintained at a temperature above 121° C. and a pressure above 1 bar above atmospheric pressure for at least 12 minutes, such as 15 minutes. As the skilled person will understand, a longer duration may be used.

An advantage of the present method resides in its safety, since the liquid used for sterilization does not add any potentially harmful chemicals to the packed chromatography column. Thus, the liquid is aqueous, such as pure or substantially pure water. However, for most chromatographic applications, the column is equilibrated with a suitable buffer before use. Thus, to provide a sterile chromatography column which is ready for use, in an advantageous embodiment of the present method, the aqueous liquid is a buffer. In this embodiment, the buffer may be any buffer commonly used in chromatography, such as PBS or Tris buffer, possibly containing appropriate salts such as NaCl.

As appears from the above, the aqueous liquid is passed through the column, which is commonly shaped as a tube. Thus, in one embodiment, the flow through the column is axial, and the aqueous liquid is then added to one end of the column, i.e. at the inlet, and withdrawn at an end substantially opposite the inlet, i.e. at the outlet. In an alternative embodiment, the flow through the column is radial, and the aqueous liquid is then added to the centre of the column and withdrawn at the periphery of the column. The passage through the column may be obtained by pumping; by gravity or by a pressure differential.

As appears from the above, the sterilization of a packed chromatography column is achieved according to the invention by a superheated aqueous liquid. In a simple embodiment, a pressurised packed chromatography column comprising chromatography matrix in aqueous liquid is heated by a heating mantle surrounding the column. Heating mantles are commonly used equipment, and available e.g. as electrical or steam heated mantles. In another embodiment, the superheated aqueous liquid is passed across the column. In order to provide the required pressure within the system, a pressure is advantageously applied before heating is initiated. In one embodiment, the method comprises a step of heating the aqueous liquid before passing it over the column. The superheating may be provided by any conventional heating device, such as a heat-exchanger or boiler.

As the skilled person in this field will understand, in order to obtain an efficient sterilization of the packed column, it is essential to maintain control of the conditions throughout the column and preferably an even flow of liquid, as controlled by measuring the asymmetry of the column packing, of an as even temperature as possible. The simplest way to monitor this is to check the temperature at the outlet of the column, to ensure that the temperature of the liquid never passes below a specified value, which is set depending on inlet temperature of the liquid, flow rate, column dimensions, packing material, contaminants to be sterilized etc. Thus, in one embodiment, the method comprises monitoring the liquid temperature at the outlet of the column. This may be achieved by a simple temperature sensor, as is well known. In one embodiment, heated liquid is passed across the packed column until the outlet temperature from the column reaches a predetermined value. Once the predetermined value has been reached, the duration of the treatment is considered to start. In the most advantageous embodiment, the liquid is heated to a higher temperature than required in the column, as the transport through piping and optionally valves etc will result in some heat loss.

To be able to control the sterilization system, the sensor preferably provides feedback to the heating or vaporising device, which in turn corrects the heating, if required. In one embodiment, the method comprises to control the liquid temperature at the inlet into the column based on the liquid temperature at the outlet. In the most advantageous embodiment, such control and liquid temperature regulation is automatic.

As is well known in this field, it is essential that a packed chromatography column maintains its uniformity during the sterilization procedure. A commonly used method to test this is to determine the plate number, and more specifically to ensure that the plate number has not changed as a result of the sterilization. In an advantageous embodiment of the invention, the plate number has changed by less than 10% as a result of the sterilization, and preferably by less than 5%. Determination of plate number is easily performed by the skilled person in this field following standard methods, see e.g. "Protein Purification" (Ed. Jan-Christer Jansson & Lars Rydén). In addition, the symmetry factor of a packed chromatography column should not change as a result of the sterilization. Thus, in one embodiment, the symmetry factor has changed by less than 1.5. The symmetry factor is easily determined from chromatograms obtained using the sterilized packed chromatography column following standard methods.

The column which is sterilized according to the present invention may be made from any suitable material known to withstand the temperature and pressure conditions used. Thus, the chromatography column may be made e.g. from a suitable plastic material, steel or glass, and may involve conventional elements such as filters, distribution means, tubing, fittings, bags etc. As the skilled person in this field will understand, it is the system as a whole i.e. column including the above suggested conventional elements that must be able to withstand the pressure and temperature conditions used.

The column may be packed with any chromatography matrix that withstands the conditions of the method, such as organic or inorganic, porous or non-porous essentially spherical particles. In an alternative embodiment, the chromatography matrix is a monolith, such as a porous monolith. Methods for packing chromatography columns are well known in this field. Examples of organic polymers commonly used as chromatographic packings are synthetic polymers, such as styrene/DVB copolymers, and natural polymers. Thus, in embodiment, the matrix is comprised of a cross-linked carbohydrate material, such as agarose, agar, cellulose, dextran, chitosan, konjac, carrageenan, gellan, alginate etc. Such matrices are easily prepared according to standard methods, such as inverse suspension gelation (S Hjertén: Biochim Biophys Acta 79(2), 393-398 (1964), or obtained from commercial sources, such as SEPHAROSE™ Fast Flow (GE Healthcare, Uppsala, Sweden).

The chromatography matrix may have been functionalised by surface modification, such as immobilisation of ligands thereon. In this context, it is understood that the term "surface" comprise both the external surfaces and the pore surfaces of a porous particle. Methods for the immobilisation of ligands to surfaces are well known in this field, see e.g. Immobilized Affinity Ligand Techniques, Hermanson et al, Greg T. Hermanson, A. Krishna Mallia and Paul K. Smith, Academic Press, INC, 1992. Thus, in one embodiment, the surfaces of said porous particles present at least one ligand. The packing of the chromatography column sterilized by the invention may comprise any kind of ligand, which is capable of withstanding the sterilization by superheated aqueous liquid used in the present method. Thus, the ligands should not comprise functional groups, structures or bonds that are sensitive to the temperature and/or pressure conditions of the present sterilization. For example, some peptide bonds may present certain sensitivity to increased temperature and/or pressure. Thus, in a specific embodiment, the ligand(s) do not comprise peptide bonds. Some nucleic acids may also be sensitive to the temperature and/or pressure conditions of the present sterilization, and are accordingly avoided as ligands on the resin packed in the chromatography column sterilized according to the invention. Thus, in an alternative embodiment, the ligands do not comprise any nucleic acids that are sensitive to the temperature and/or pressure conditions of the present method. In a specific embodiment of the present method, the ligand(s) are selected from the group consisting of ion-exchange ligands; multi-modal ligands; thiophilic ligands; and hydrophobic chromatography (HIC) ligands. The ligands immobilised to the particles may have been coupled via extenders, also known as "flexible arms", such as dextran or synthetic polymers.

Thus, the present inventors show that contrary to what was stated in the above-discussed U.S. Pat. No. 5,676,837 (Jungbauer), it is possible to destroy microbes in a chromatography resin by use of heated water without impairing the resin. It has also been shown that the present method may be repeated a number of times. In addition, the present invention does not add any chemicals that could potentially impact the product which is purified on a chromatography column sterilized according to the invention. Furthermore, the present invention shows that the packing properties of the column such as its uniformity are not impaired by the treatment. This was quite unexpected in view of the above discussed U.S. Pat. No. 5,423,982 (Jungbauer et al), which suggests that specific equipment is required to avoid problems of dead zones in the packing. Contrary, the present method is applicable to any commonly used packed chromatography column, without having any serious effect on its number of plates or symmetry factor.

The present invention also includes the use of a packed chromatography column sterilized as described above for the separation of one or more biomolecules from a fluid mixture, such as a fermentation liquid. The products purified using the columns sterilized according to the invention may be drugs or drug targets; vectors for use in therapy, such as plasmids, viruses or cells for use in gene or cell therapy; feed supplements, such as functionalized food; diagnostic agents etc. A specific application of a biomolecule purified according to the invention is a drug for personalized medicine.

The use according to the invention may be a capture step, i.e. the first chromatography step in a multi step protocol. In this embodiment, the purity of the product may be as commonly obtained in capture of the biomolecule(s) in question, such as in the range of 30-80%. Alternatively, the use according to the invention may be an intermediate step in a multi step protocol. In this embodiment, the purity of the product may be as commonly obtained in intermediate purification of the biomolecule(s) in question, such as in the range of 70-95%. In another alternative, the use according to the invention may be a polishing step, i.e. the last chromatography step in a multi step protocol. In this embodiment, the purity of the product may be as commonly obtained in polishing of the biomolecule(s) in question, such as in the range of 95-99.5%, and preferably above 99.5%.

In a specific embodiment, the present use is a multistep protocol, wherein the end product is virus and/or plasmid DNA obtained as substantially pure products. In this context, "substantially pure" means a purity of at least about 98%, such as at least about 99% and preferably at least about 99.5%. This embodiment may comprise other process steps in addition to the use of a sterilized packed chromatography column, such as discussed below in the context of a system sterilized according to the invention.

In a second aspect, the present invention relates to a system for sterilizing a chromatography column, which comprises a liquid reservoir; a heating device; at least one packed chromatography column; and at least one temperature sensor, which is preferably located at the outlet of chromatography column. The system has been sealed according to well known methods to allow maintenance of a fixed pressure therein. In one embodiment, the system also comprises one or more pumps and/or tubing. The packed chromatography column may be any kind of chromatography column, e.g. as discussed above. In one embodiment, the packed chromatography column is known as a limited-use chromatography column, which in this context means a packed chromatography column which is most suitable for a limited number of uses, such as 1-10 uses. Such limited-use products are commercially known as "disposable products".

The liquid reservoir may comprise any of the above-discussed aqueous liquids, such as water or an aqueous buffer, which is to be used in superheated form to sterilize the system. Thus, in one embodiment, the heating device is connected to said device in a fashion that allows warming of the aqueous liquid to a desired temperature. In one embodiment, the heating device is a heat exchanger or a boiler. The chromatography column and its packing may be any one of the above-described embodiments. The present invention also comprises the sterilization of a system, such as the one described above, by passing a superheated aqueous liquid through said system. In one embodiment, the system comprises at least one packed chromatography column; and one or more further components selected from the group consisting of filters; vessels; liquids, such as buffers; and centrifuges. In a specific embodiment, the present system is connected to a fermenter, which may have been separately sterilized in an autoclave. In this embodiment, the superheated aqueous liquid is added to the system at any point downstream of the fermenter.

In a specific embodiment, the present invention is a method of sterilizing a kit of components, which components are either arranged separately or assembled together in a format suitable for use with a specific control unit. Such a kit may comprise two or more of the components selected from the group consisting of filters; vessels; and centrifuges.

In a specific embodiment, the system comprises automated means for control of the temperature and/or pressure used in the sterilization process. Such control is provided as discussed above, preferably by aid of a computer. Units for control of this kind of operations are well known to the person skilled in this field.

The system sterilized according to the present invention may be used to purify under sterile conditions any product such as biomolecules, e.g. proteins, peptides, nucleic acids, virus, cells etc. One advantage of the system is that it is applicable with larger molecules as well, such as large viruses and nucleic acids, which are more difficult to be sterile-filtered in currently used processes for the preparation of biomolecules.

In a third aspect, the present invention relates to a packed chromatography column, which has been sterilized in packed state and which comprises no traces of added sterilizing chemicals. Thus, the column is substantially free from potentially harmful chemicals. The column may be made from any of the materials discussed above, and may comprise any one of the above-discussed packings. Further, the sterile column according to the invention may comprise tubing and fittings suitable for attachment to a chromatography system. The method according to the invention was used to sterilize the packed column of this aspect. In a specific embodiment, the sterile packed chromatography column is known as a limited-use chromatography column, which in this context means a packed chromatography column which is most suitable for a limited number of uses, such as 1-10 uses. Such limited-use products are commercially known as "disposable products".

Finally, the invention also encompasses a method of cleaning a packed chromatography column, wherein the packing of the column comprises a separation matrix comprised of particles, which method comprises heating an aqueous liquid to a temperature which under the prevailing pressure provides a superheated aqueous liquid; and passing said superheated aqueous liquid through the packing of the column to obtain at least one substantially sterile packed chromatography column. The discussion above with regard to suitable liquids, chromatography columns and packings, and instrumentation applies equally well to this embodiment. The cleaning according to the invention may be used as an alternative to the conventionally used cleaning in place (cip) protocols, which commonly uses 0.1-1M NaOH, pH 14. This will allow short production cycles of column sterilization in sample loading buffer, sample loading and finally target molecule elution after which the cycle can start again.

EXAMPLES

The following examples are provided for illustrative purposes only, and should not be construed as limiting the scope of the present invention as defined in the appended claims.

Example 1

Sterilization of Media

Sterilisation according to the invention was here tested on two separation media; SEPHAROSE™ 4 Fast Flow and ANX SEPHAROSE™ 4 Fast Flow (both GE Healthcare, Uppsala, Sweden).

SEPHAROSE™ 4 Fast Flow consists of cross linked agarose and ANX SEPHAROSE™ 4 Fast Flow consists of SEPHAROSE™ 4 Fast Flow with highly substituted diethyl aminoethylene. When sterilising ANX SEPHAROSE™ 4 Fast Flow, a counter ion was used in the mobile phase to avoid hydrolysis of the medium.

Figure 1:
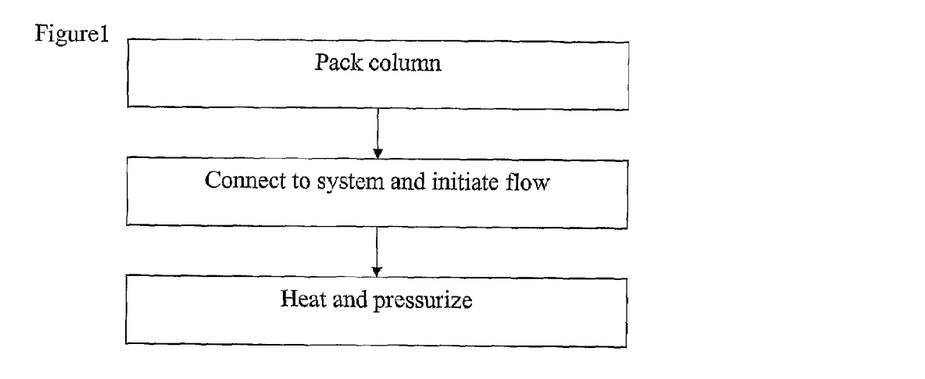
FIG. 1 shows the process according to the invention schematically. In brief.
Figure 2:
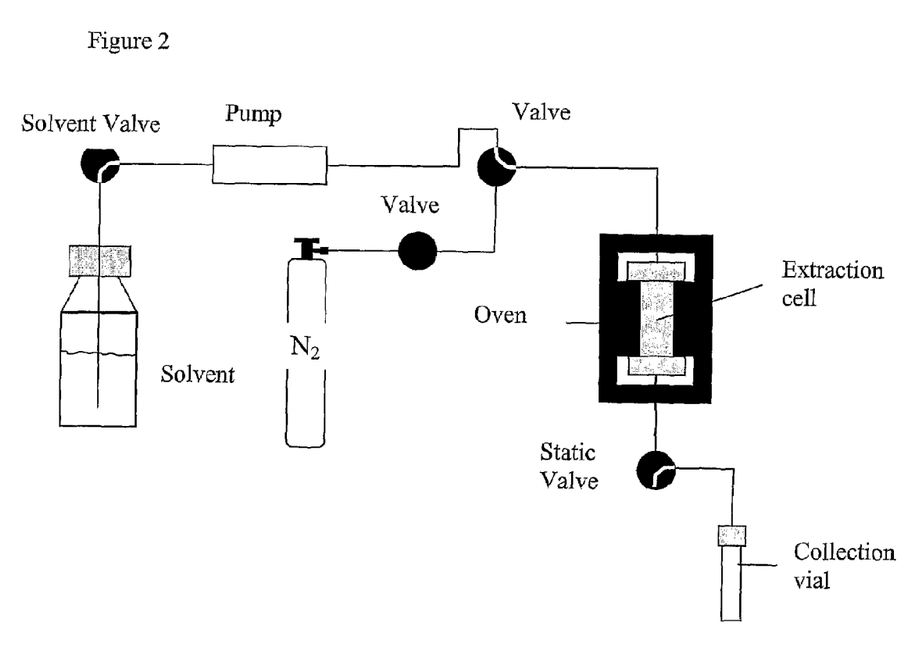
FIG. 2 shows schematically the equipment used in example 1 below. In brief.

Short description of sterilisation technique:

The media were exposed to pressurised fluid extraction (PFE), here named Accelerated Solvent Extraction (ASE). In ASE, the medium is packed into a cell, the cell is filled with solvent, the cell is then heated and pressurised, the heat and pressure is held for a specified time, clean solvent is pumped into the cell and finally the solvent is purged from the cell with $N_2$ gas as shown in FIG. 2.

Instrumental

| | |
|---|---|
| Accelerated Solvent Extractor | ASE 200 system from Dionex |
| Extraction cell, 33 mL, | Dionex |
| Aerosol tight vials | Dionex |
| Glass filter, G3, 500 mL | Scott Duran |
| Balance | |
| pH meter | Radiometer |

Sample Pre-Treatment and Cell Packing

For ANX SEPHAROSE™ 4 Fast Flow (HS) 0.1 M Tris (hydroxymethyl) aminomethan/HCl was used as the mobile phase and for SEPHAROSE™ 4 Fast Flow 0.1 M NaCl was used.

1 Approximately 50 mL sedimented media was washed with 5×50 ml of appropriate buffer, 0.1 M Tris (hydroxylmethyl) aminomethane/HCl and 0.1 M NaCl, respectively, on a G3 glass filter.
2 The gel was transferred into a beaker and diluted with the actual buffer to obtain a 50% gel mixture.
3 The 33 mL extraction cell was then packed.

Sterilization/Extraction

The packed cell was placed into the ASE cell holder. Appropriate buffer was placed in the solvent holder. The system was rinsed with the actual solvent three times. 25 sample vials was placed in the sample holder. 3 rinse vials were also placed in the rinse positions of the cell holder.

Below the method parameters used for the sterilisation (extraction) are given.

The cell volume was 33 ml.
The oven temperature was 121° C.
The pressure was 34.5 minutes.
The time at these conditions was 12 minutes.

The heat time was 6 minutes.
The wash volume was 90% of the cell volume.
Nitrogen purging was done for 20 seconds.
The number of cycles was 1.
The sterilization procedure was repeated 25 times.

Example 2

Flow/Pressure Analysis of ASE Treated Media and Non-Treated Media

Materials

| | | |
|---|---|---|
| Column | XK 16/10 | GE Healthcare |
| Pump | P-900 | GE Healthcare |
| Pressure manometer | 0-10 bar, ser no 3,771,719 | Wika Alexander W. GmbH |
| Digital pressure gauge | ser no 3,741,280 | Wika Alexander W. GmbH |
| Glass filter | G3 pore size | Scott Duran |

Performance 25 mL ASE treated media, ANX SEPHAROSE™ 4 Fast Flow (HS) T-304627 and SEPHAROSE™ 4 Fast Flow T-302447, were washed separately with 10 cv 0.1 M NaCl on a G3 glass filter. The gel mixtures were poured into a XK 16/10 column and the gel was settled. The gel mixture was added into the column until a gel height of 10.5 cm was obtained. A top adaptor was mounted and the gel was packed at a flow rate of 2 mL/min with 0.1 M NaCl as mobile phase. The gel-height was adjusted to 100±1 mm at 2 mL/min. The Flow/pressure test with 0.1 M NaCl was performed according to Table 2. The pressure at each flow rate was monitored and noted. The column was equilibrated for 5 minutes between each measure point.

The flow rates at which the pressures were monitored were 5, 7, 10, 12, 15, 20, 25, 27, 30 and 35 ml/min.

Non-ASE treated media, ANX SEPHAROSE™ 4 Fast Flow (HS) T-304627 and SEPHAROSE™ 4FF T-302447, were tested with the procedure described above. After all media have been flow/pressure tested a back-ground pressure test with the same flow properties was performed with only 0.1 M NaCl (no medium in the column).

Results

Figure 3A:
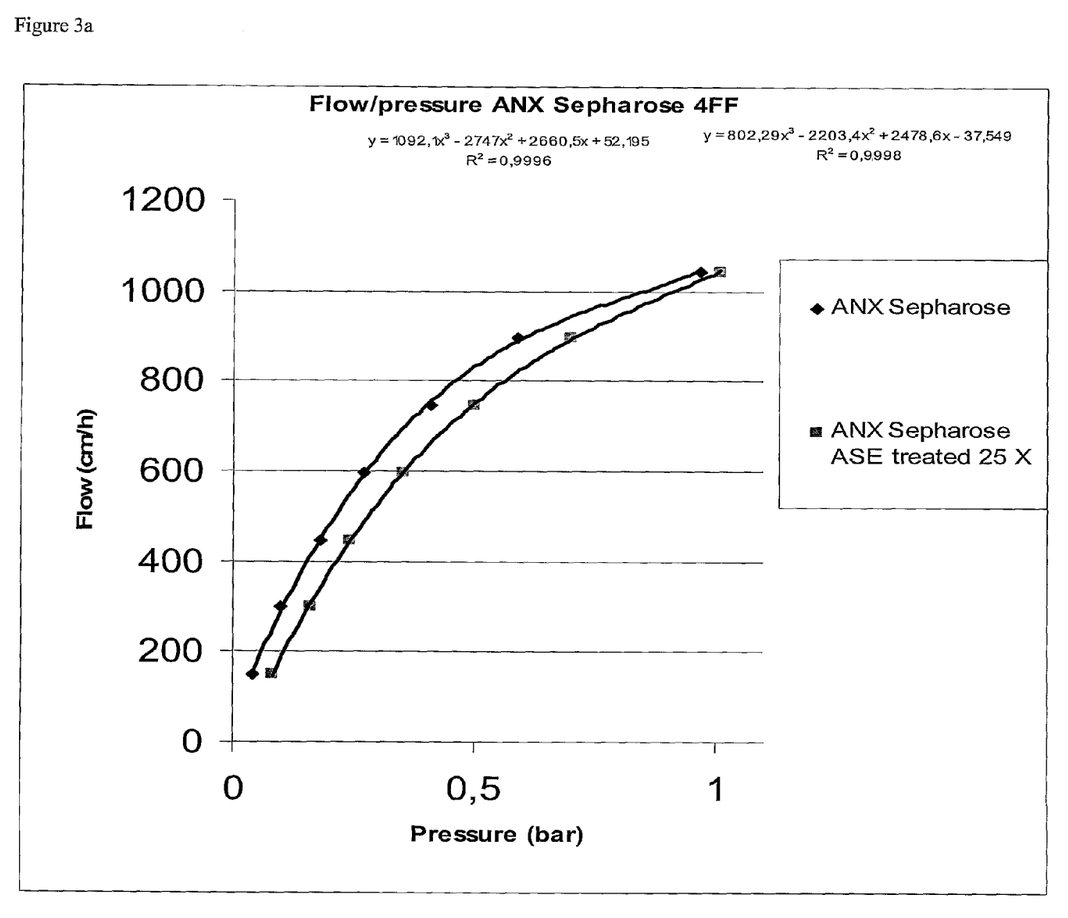
FIG. 3a shows the results from the flow/pressure test of sterilized and non-sterilized ANX SEPHAROSE™ 4 Fast Flow. The pressure in bar is given on the x-axis and the flow in cm/h on the y-axis. The upper curve (diamonds) shows the result from the medium before sterilizing and the lower curve (squares) shows the results from the sterilized medium. As appears clearly, sterilization according to the invention has not affected the matrix to any substantial extent.
Figure 3B:
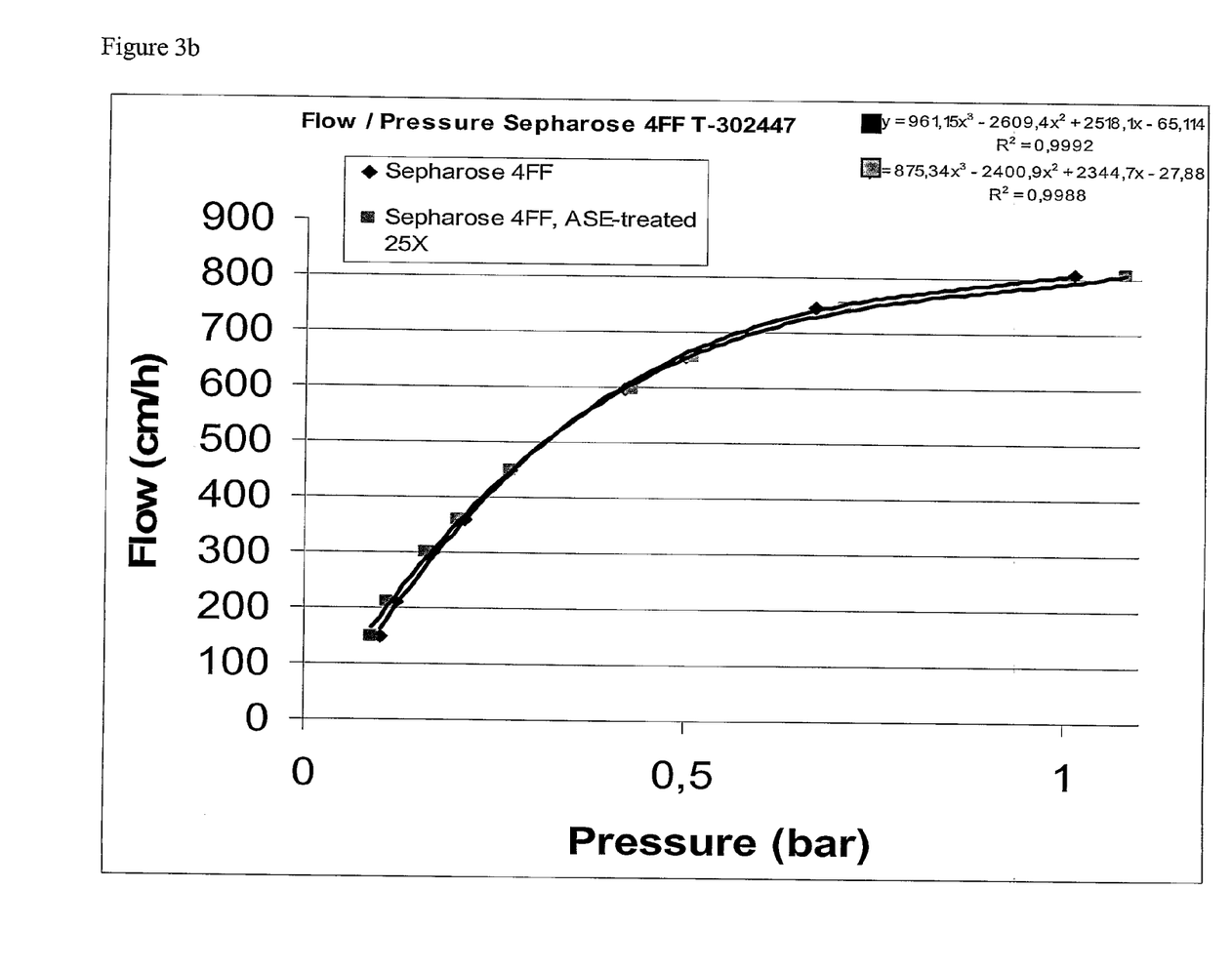
FIG. 3b shows the results from the flow/pressure test of sterilized and non-sterilized SEPHAROSE™ 4 Fast Flow. The pressure in bar is given on the x-axis and the flow in cm/h on the y-axis. The upper curve (diamonds) shows the result from the non-sterilized medium and the lower curve (squares) shows the results from the sterilized medium. As appears clearly, sterilization according to the invention has not affected the matrix to any substantial extent.

The results are shown in FIGS. 3a and 3b. As appears clearly in FIGS. 3a and 3b, sterilization according to the invention has not affected the matrix to any substantial degree.

Example 3

Function Test of ANX SEPHAROSE™ 4 Fast Flow

Performance

Regular and sterilized (ASE-treated) ANX SEPHAROSE™ 4 Fast Flow were packed in 4.6/50 PEEK columns, at flow rates of 2 ml/min (2 bar) during 15 minutes. Height Equivalent Theoretical Plates (HETP) was determined with 10 ul 2M NaCl at 0.2 ml/min. Next, the columns were calibrated in 20 mM Piperazine pH 6.2 at 0.1 ml/min and 100 microliter sample, containing the model proteins Gammabind (4 mg/mL), beta-lactoglobulin A (11 mg/mL) and beta-lactoglobulin B (11 mg/mL) in 20 mM Piperazine pH 6.2, was loaded on the column. Elution was performed by a linear gradient to 0.30M NaCl, 20 mM Piperazine pH 6.2 over 21 column volumes.

Results

Figure 4:
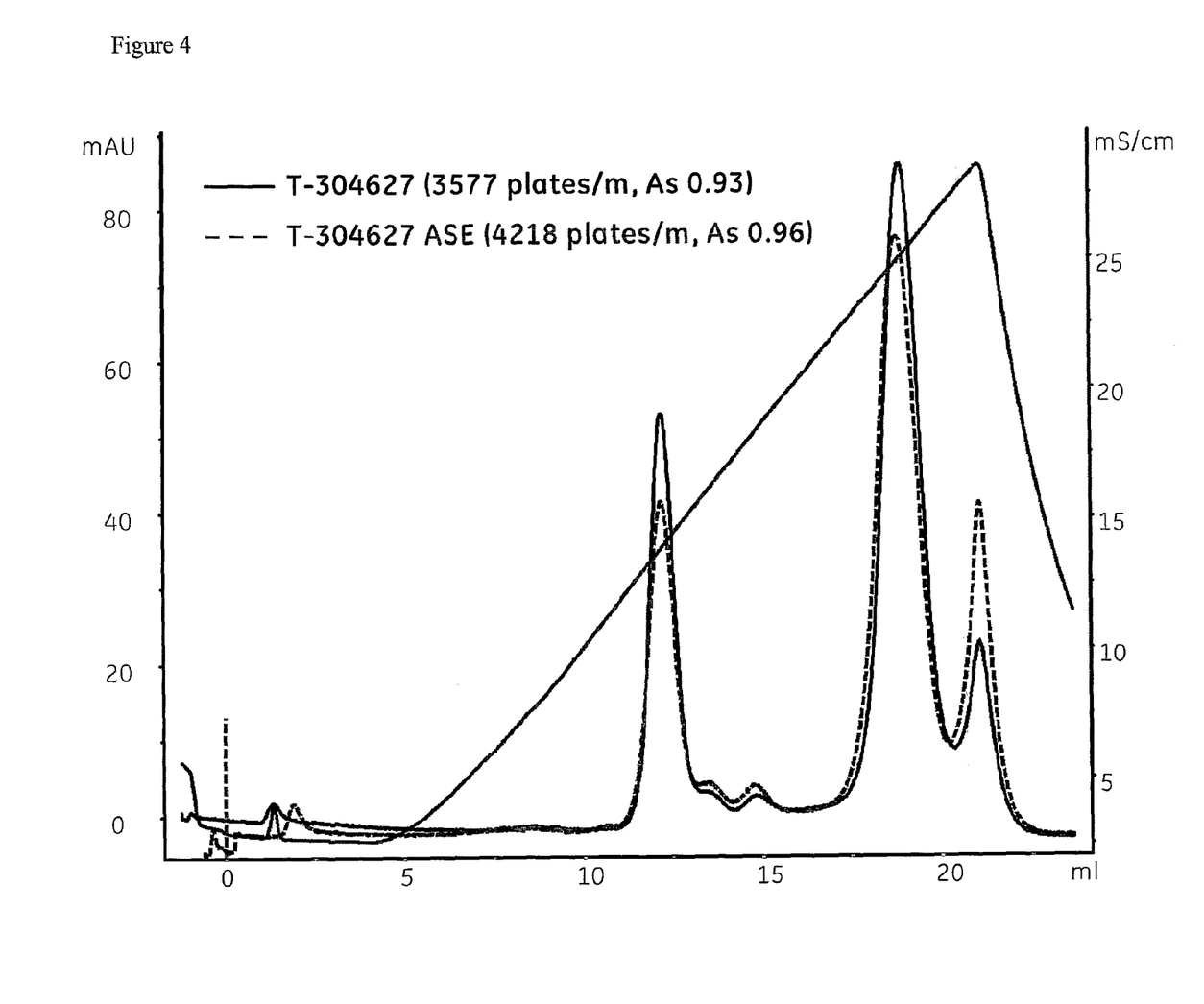
FIG. 4 shows results from the function test on ASE-treated ANX SEPHAROSE™ 4 Fast Flow and untreated ANX SEPHAROSE™ 4 Fast Flow as described in example 3. The elution volume is given on the x-axis in ml, UV absorbance in mAU is given on the left y-axis and conductivity in mS/cm on the right y-axis.

Results are shown in FIG. 4. As appears clearly from FIG. 4, sterilization according to the invention has not affected the function of the medium to any substantial extent.

Example 4

Determination of Chloride Ion Capacity of ANX SEPHAROSE™ 4FF

Instrumental

| Titroprocessor | Metrohm Titrando |
|---|---|
| Combined Ag-electrode | Scott Duran |
| Titration vessels, 80 ml | |
| Glass filters G3 pore size 3.735 ml cube | Scott Duran |

Performance 10 mL of the ASE treated ANX SEPHAROSE™ 4 Fast Flow (HS) T-304627 was washed with 10×10 mL milli-Q water on a G3 glass filter. The washed gel was transferred into a beaker and it was diluted with milli-Q water until a 50% gel-mixture was obtained. A 3.735 mL "cube" was used for sample out-take. The gel-mixture was poured into the "cube" and vacuum suction was applied for one minute. The vacuum suctioned gel in the "cube" was transferred into a G3 glass-filter. A duplicate analysis was performed. 2×20 mL 0.1 M HCl was added into the glass filters. The excess of $Cl^-$ was removed with 5×0.001 M HCl. The gel was vacuum suctioned for two minutes and transferred quantitatively into titration vessels with ~80 mL 0.1 M $NaNO_3$. Few drops of HNO3 were added into each titration vessel. Each titration vessel was titrated with 0.0999 M $AgNO_3$ to the equivalence point. The non ASE treated ANX SEPHAROSE™ 4 Fast Flow (HS) T-304627 was treated and titrated as the ASE treated medium.

Results

Table shows the chloride ion capacity results. As appears clearly from the Table 1, sterilization according to the invention has not affected the medium to any substantial extent.

TABLE 1

Chloride ion capacity of ANX SEPHAROSE ™ 4 FF (HS) T-304627, ASE-treated and non-ASE-treated.

| Sample | Vc | C 0.1 M $AgNO_3$ | V $AgNO_3$ | Capacity mmol/ mL gel | Capacity Average mmol/mL gel |
|---|---|---|---|---|---|
| ANX ASE treated | 3.735 | 0.0999 | 6.0903 | 0.162897 | |
| ANX ASE treated | 3.735 | 0.0999 | 6.3411 | 0.169605 | 0.166 |
| ANX Reference | 3.735 | 0.0999 | 6.1714 | 0.165066 | |
| ANX Reference | 3.735 | 0.0999 | 6.2296 | 0.166623 | 0.166 |

Example 5

Packing and Sterilization of a Column

Figure 5:
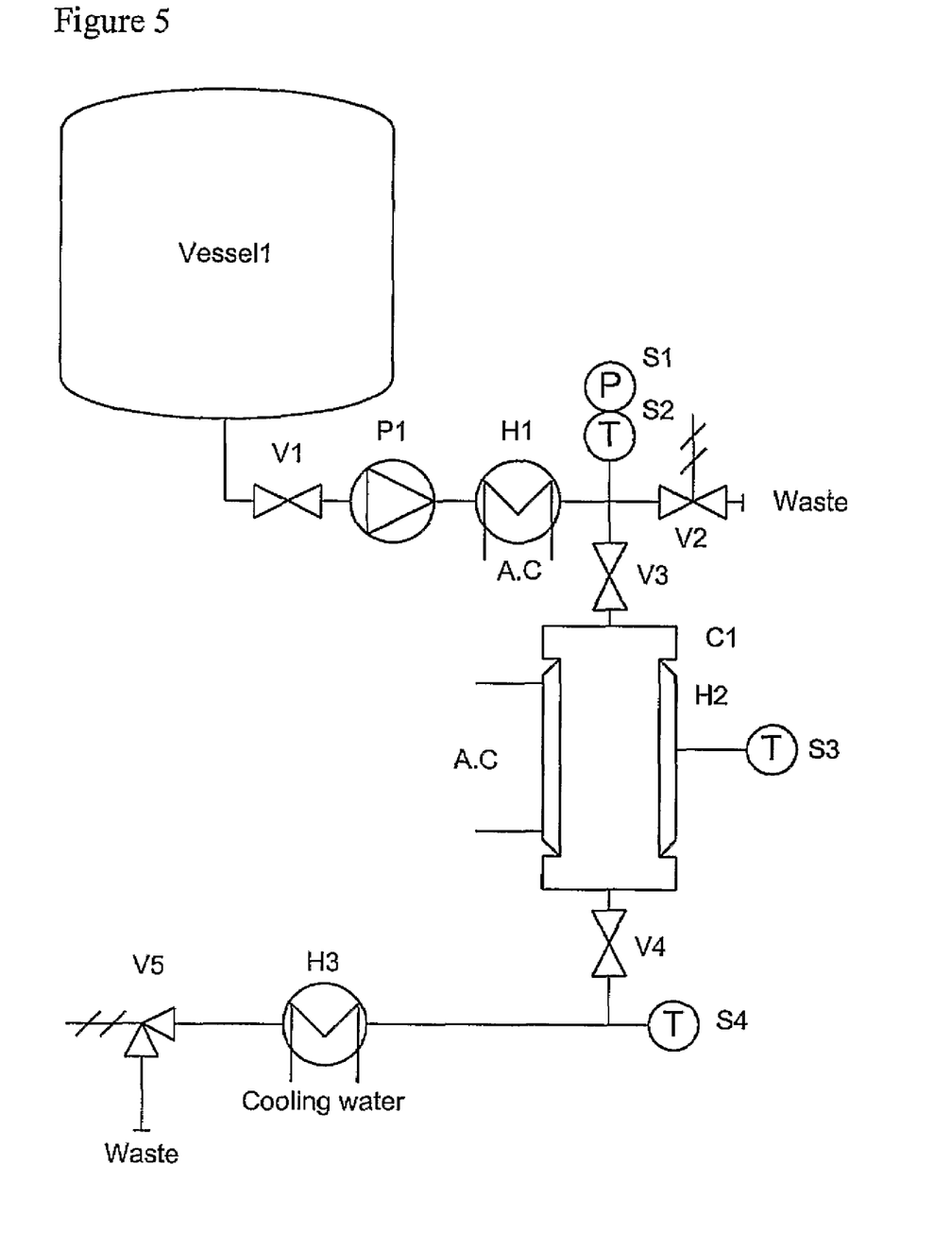

The system used in this example is shown in FIG. 5. Sterilization according to invention was here tested on one separation media: SEPHAROSE™ 4 Fast Flow (GE Healthcare, Uppsala, Sweden). The media was packed in a Fine Line 100 column (GE Healthcare) equipped with an electrical heating jacket. Media corresponding to a sedimented bed height of 12 cm was poured into the column and suspended in enough purified water (PW) to fill the column. The column adaptor was immersed in the suspension to avoid getting air trapped beneath it. The adaptor was lowered at a speed of 60 cm/h and the excessive PW was drained through the bottom of the column. When the packed media had reached a bed height of 10 cm the packing was aborted. The HETP was tested according to example 6. The column was connected to the system according to FIG. 5. Saline solution (0.1 M $NaSO_4$) was pumped through the column (120 ml/min, 90 cm/h) throughout the sterilization process. The heating power was switched on and when temperature on the outlet of the column reached 121° C. the process was run for an additional 20 min then the heating power was turned off. The system was left too cool down still with the flow going through the column. As the column reached room temperature the HETP was tested again.

Example 6

Figure 6:
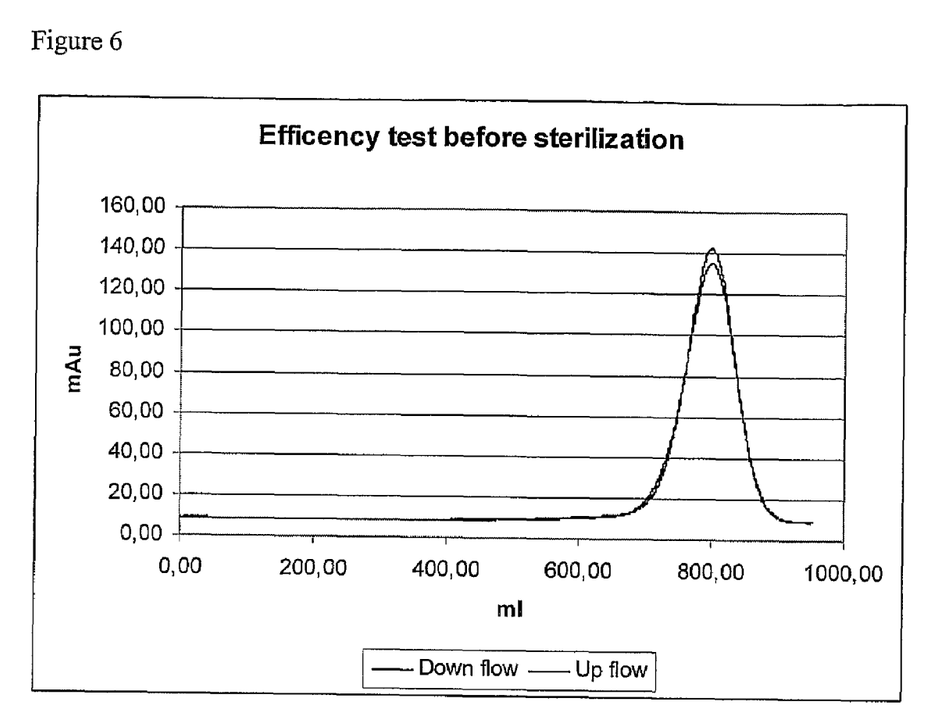
FIG. 6 shows the results of the testing of properties of a packed column before treatment according to the invention, as described in Example 6. Down flow: 4732 plates per meter and 0.83 in asymmetry. Up flow: 5138 plates per meter and 0.87 in asymmetry.
Figure 7:
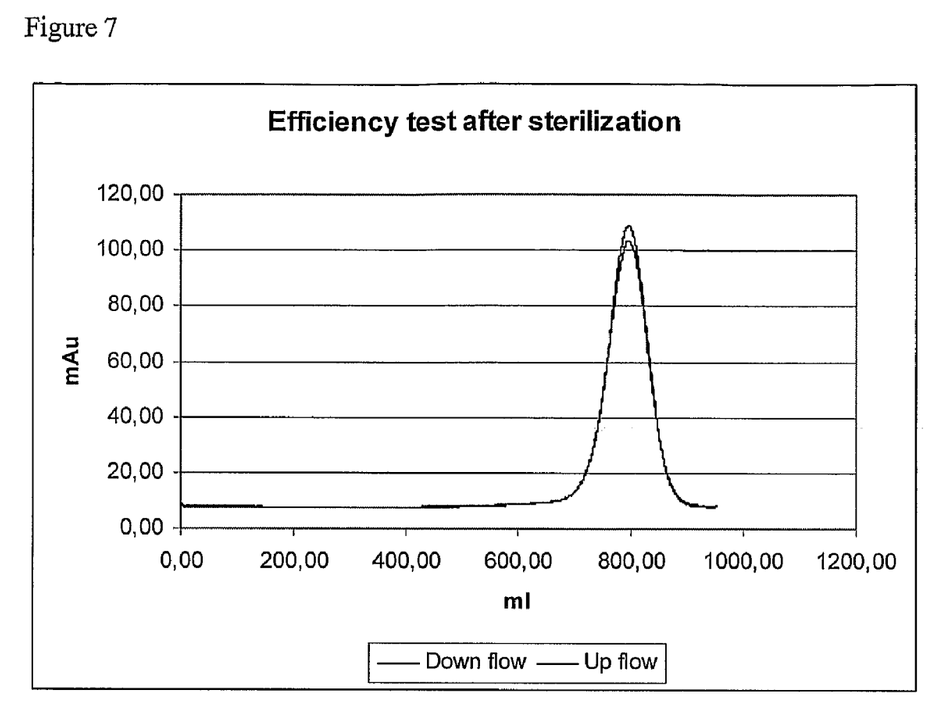
FIG. 7 shows the results of the testing of properties of a packed column after sterilization, as described in Example 6. Down flow: 5777 plates per meter and 0.89 in asymmetry. Up flow: 5574 plates per meter and 0.88 in asymmetry. As appears from FIGS. 6 and 7, the sterilization has no negative effect on the packed media.

HETP Testing of Column 0.01 column volumes of 2% Acetone was injected to the column treated as described in Example 5 above and eluted with purified water (PW) at a flow rate of 30 cm/h. The UV trace at 280 nm was followed and used for evaluation. The liquid was injected with up-flow and down-flow. The results are shown in FIGS. 6 and 7.

The above examples illustrate specific aspects of the present invention and are not intended to limit the scope thereof in any respect and should not be so construed. Those skilled in the art having the benefit of the teachings of the present invention as set forth above, can effect numerous modifications thereto. These modifications are to be construed as being encompassed within the scope of the present invention as set forth in the appended claims.

What is claimed is:

1. A method of sterilizing at least one chromatography column packed with a separation matrix, comprising:
providing a sealed chromatography column made from a material which withstands the temperature and pressure conditions used;
applying a pressure over the chromatography column;
heating an aqueous liquid which is a buffer commonly used in chromatography to a temperature which under the prevailing pressure provides a superheated aqueous liquid; and
passing said superheated aqueous liquid through the packing of said column(s) to obtain at least one substantially sterile packed chromatography column, wherein the temperature and pressure of the superheated aqueous liquid are substantially maintained throughout the column such that said aqueous liquid is maintained superheated.

2. The method of claim 1, wherein the superheated aqueous liquid is passed through the packing of the column in a substantially uniform flow.

3. The method of claim 1, wherein the superheated aqueous liquid is added to an inlet at one end of the packed chromatography column and withdrawn at an outlet located substantially opposite to the inlet.

4. The method of claim 1, wherein the superheated aqueous liquid is added to the centre of the packed chromatography column and withdrawn at the periphery of the packed chromatography column.

5. The method of claim 1, wherein the liquid is pumped from a heater to the chromatography column and/or through the chromatography column.

6. The method of claim 1, further comprising monitoring the aqueous liquid temperature at an outlet of the column.

7. The method of claim 6, further comprising controlling the temperature at an inlet into the column based on the temperature at the outlet.

8. The method of claim 1, wherein the matrix is comprised of porous particles.

9. The method of claim 1, wherein the matrix is comprised of cross-linked polysaccharide particles.

10. The method of claim 1, wherein the matrix is comprised of synthetic polymer particles.

11. The method of claim 1, wherein the matrix is comprised of monolithic material.

12. The method of claim 8, wherein the surfaces of said porous particles present at least one ligand.

13. The method of claim 12, wherein the ligand(s) are substantially devoid of heat-sensitive peptide bonds.

14. The method of claim 12, wherein the ligand(s) are selected from the group consisting of ion-exchange ligands, multimodal ligands, thiophilic ligands and hydrophobic chromatography (HIC) ligands.

* * * * *